(12) United States Patent
Harms (10) Patent No.: US 12,005,230 B2
(45) Date of Patent: Jun. 11, 2024

(54) DRIVE UNIT FOR A LIQUID HANDLING DEVICE AND LIQUID HANDLING DEVICE

(71) Applicant: SANOFI, Paris (FR)

(72) Inventor: Michael Harms, Frankfurt am Main (DE)

(73) Assignee: Sanofi, Paris (FR)

(*) Notice: Subject to any disclaimer, the term of this patent is extended or adjusted under 35 U.S.C. 154(b) by 855 days.

(21) Appl. No.: 17/054,378

(22) PCT Filed: May 13, 2019

(86) PCT No.: PCT/EP2019/062136
§ 371 (c)(1),
(2) Date: Nov. 10, 2020

(87) PCT Pub. No.: WO2019/219564
PCT Pub. Date: Nov. 21, 2019

(65) Prior Publication Data
US 2021/0220554 A1 Jul. 22, 2021

(30) Foreign Application Priority Data
May 15, 2018 (EP) ..................... 18305593

(51) Int. Cl.
*A61M 5/145* (2006.01)
*A61M 5/142* (2006.01)

(52) U.S. Cl.
CPC .... *A61M 5/14566* (2013.01); *A61M 5/14248* (2013.01); *A61M 2005/14268* (2013.01); *A61M 2205/8206* (2013.01)

(58) Field of Classification Search
CPC .......... A61M 5/14546; A61M 5/14248; A61M 5/1456; A61M 5/1413; A61M 5/14566;
(Continued)

(56) References Cited

U.S. PATENT DOCUMENTS

| 4,157,716 A | 6/1979 | Ruegg |
| 7,063,684 B2 | 6/2006 | Moberg |

(Continued)

FOREIGN PATENT DOCUMENTS

| CN | 101631578 | 1/2010 |
| CN | 104411350 | 3/2015 |

(Continued)

OTHER PUBLICATIONS

PCT International Preliminary Report on Patentability in International Application No. PCT/EP2019/062136, dated Nov. 17, 2020, 7 pages.

(Continued)

*Primary Examiner* — Tiffany Legette
(74) *Attorney, Agent, or Firm* — Fish & Richardson P.C.

(57) ABSTRACT

A drive unit for a medical device includes a drive unit housing, a drive member retained in the drive unit housing and movable relative to the drive unit housing to drive an operation of the medical device, the drive member includes a coupler output portion configured to be operatively connected to a liquid handling unit, a drive mechanism retained in the drive unit housing, wherein the drive mechanism is coupleable or coupled to the drive member via a mechanism interface and is configured to transfer a driving force or torque to the drive member, and a sealing member provided to establish a sealed interface with the drive member, wherein the sealed interface defines a sealed section of the interior of the drive unit housing, wherein the mechanism interface is arranged within the sealed section and the coupler output portion is arranged outside of the sealed section.

21 Claims, 6 Drawing Sheets

(58) Field of Classification Search
CPC ......... A61M 2005/14268; A61M 2005/14264; A61M 2205/103; A61M 2205/8206
See application file for complete search history.

(56) References Cited

U.S. PATENT DOCUMENTS

| 7,273,472 | B2 | 9/2007 | Peter et al. |
| 2003/0167039 | A1 | 9/2003 | Moberg |
| 2008/0051697 | A1* | 2/2008 | Mounce ............ A61M 5/14232 604/32 |
| 2016/0287788 | A1 | 10/2016 | Tremblay et al. |

FOREIGN PATENT DOCUMENTS

| CN | 105833390 | 8/2016 |
| EP | 2066372 | 6/2009 |
| JP | H03-56844 U | 5/1991 |
| JP | H08-296742 | 11/1996 |
| JP | 2010-501282 | 1/2010 |
| JP | 2010-526633 | 8/2010 |
| JP | 2010-535057 | 11/2010 |
| WO | WO 2008/024812 | 2/2008 |
| WO | WO 2008/139458 | 11/2008 |
| WO | WO 2009/016636 | 2/2009 |
| WO | WO 2009/132777 | 11/2009 |
| WO | WO 2014/008393 | 1/2014 |
| WO | WO 2014/154777 | 10/2014 |
| WO | WO 2018/083062 | 5/2018 |

OTHER PUBLICATIONS

PCT International Search Report and Written Opinion in International Application No. PCT/EP2019/062136, dated Aug. 7, 2019, 12 pages.

* cited by examiner

DRIVE UNIT FOR A LIQUID HANDLING DEVICE AND LIQUID HANDLING DEVICE

CROSS REFERENCE TO RELATED APPLICATIONS

The present application is the national stage entry of International Patent Application No. PCT/EP2019/062136, filed on May 13, 2019, and claims priority to application Ser. No. 18/305,593.8, filed on May 15, 2018, the disclosures of which are incorporated herein by reference.

TECHNICAL FIELD

The present disclosure relates to a drive unit for a liquid handling device, such as a medical device, in particular a drug delivery device. Furthermore, the disclosure relates to a liquid handling device and/or medical device, in particular a drug delivery device, with such a drive unit.

BACKGROUND

The present disclosure describes an improved drive unit for a liquid handling device and/or for a medical device, such as a drug delivery device. Furthermore, the present disclosure describes an improved liquid handling device and/or medical device, in particular a drug delivery device.

SUMMARY

One aspect of the present disclosure relates to a drive unit for a liquid handling device, such as a medical device, in particular a drug delivery device. Another aspect of the disclosure relates to a liquid handling device and/or a medical device, in particular a drug delivery device, comprising the drive unit. The device may comprise the drive unit and a liquid handling unit. The liquid handling unit may be secured to the drive unit, for example releasably. The liquid handling may form a disposable item or unit. The drive unit may be reused. The device may be a dispensing device, where liquid is dispensed from the device, and/or a retrieving or suction device, where liquid substance is sucked into the device from the exterior of the device.

It should be noted that, herein, features relating to the drive unit do also apply for the device comprising the drive unit and vice versa. That is to say, if a feature is disclosed in conjunction with the device, for example, it should also be regarded as being disclosed for the drive unit without referencing the other features of the device. Moreover, features discussed in conjunction with different aspects or embodiments may be combined with one another, even if such a combination is not explicitly disclosed.

In an embodiment, the drive unit comprises a drive unit housing and a drive member, which is retained in the drive unit housing and moveable relative to the drive unit housing to drive an operation of the device. The drive member comprises a coupler output portion. The coupler output portion is expediently configured to be operatively connected to a liquid handling unit, e.g. to a coupler input portion of the liquid handling unit. The coupler output portion may have a free end. The liquid handling unit may be part of the device. The coupler output portion may define the interface, e.g. provide one or more mechanical coupling features, for coupling the drive unit to the liquid handling unit. The coupler output portion of the drive member may be formed as a separate part or unitary with the remaining drive member. That is to say, the drive member may have a plurality of parts, e.g. two parts, such as a drive shaft and a coupling member, or be unitary. If the drive member has a plurality of parts, the parts are preferably rigidly connected such that the drive member acts as a single member. When the liquid handling unit is operatively connected to the drive unit, e.g. when the device has been assembled, the coupler output portion may be coupled to the coupler input portion of the liquid handling unit to transfer movement, force and/or torque from the drive member to the liquid handling unit. The coupler output portion may be rotationally and/or axially locked to the coupler input portion, such that movement of the drive member may be transferred from the drive unit to the liquid handling unit. The movement transferred from the drive member to the liquid handling unit may be used to manipulate liquid in the liquid handling unit. The coupler input portion of the liquid handling unit may be a pump driver coupling portion, which provides a coupling between the drive member and a pump driver of the liquid handling unit. The pump driver may be configured to drive a pumping action in the liquid handling unit. The pump driver may be configured to move liquid within the liquid handling unit. When the drive member and the liquid handling unit are operatively connected, the drive unit housing may be, preferably releasably, secured to a liquid handling unit housing of the liquid handling unit.

Further, a drive mechanism is retained in the drive unit housing. The drive mechanism is coupled to or coupleable to the drive member via a mechanism interface. The drive mechanism is configured to transfer a driving force or torque from the mechanism to the drive member. The transfer of the force or torque may occur via the mechanism interface. The drive member may, for example, be a drive shaft or comprise a drive shaft.

The drive unit, furthermore, comprises a sealing member. The sealing member is preferably provided to establish a sealed interface with the drive member. The sealing member may sealingly engage the drive member. For example, the sealing member may have a sealing lip, which engages the drive member to provide a sealed interface with the drive member. The sealed interface may define or limit a sealed section of an interior of the drive unit housing. The coupler output portion is expediently arranged outside of the sealed section. In this way, it may provide the interface to the liquid handling unit. The mechanism interface between drive member and drive mechanism is preferably arranged within the sealed section. Not only the mechanism interface but the entire drive mechanism and, if required, an energy or power source for providing energy to drive the drive mechanism may be provided in the drive unit housing and, particularly, in the sealed section. By providing the sealing member, which establishes a sealed interface with the drive member, it is ensured that elements of the drive unit, which are arranged in the sealed section of the drive unit housing, are protected against environmental influences, such as moisture, dirt, and/or dust. The sealed interface may be moisture-tight, water-tight, water jet-tight, and/or dust-tight.

Thus, that element, which transmits movement to an element in the liquid handling unit, i.e. the drive member, is guided from the sealed section of the drive unit housing to the outside of the sealed section across the sealing member and is available to provide a, preferably mechanical, interface to the liquid handling unit. The remaining portions of the interior of the drive unit housing may be sealed properly.

In an embodiment, the drive member is moveable, e.g. axially and/or rotationally, relative to the sealing member. The drive member may be, e.g. axially, moveable relative to the sealing member from a first position to a second position and/or vice versa. The drive member may be in the second position, when the coupler output portion is operatively connected to the coupler input portion of the liquid handling unit. The drive member may be in the first position, when the entire liquid handling unit and/or its coupler input portion is disconnected from the drive unit. When the drive unit is being operatively coupled to the liquid handling unit, the drive member may be moved away from the first position towards the second position. In the second position, the drive unit and the liquid handling unit may be coupled.

Accordingly, the drive member may be axially moveable when the coupling to said liquid handling unit is being established. This movement may be towards the sealing member as seen from the coupler output portion. Consequently, in the second position, the section of the drive member which is arranged in the sealed section of the drive unit housing may be longer than the one which is arranged in the sealed section in the first position.

In an embodiment, the drive unit comprises a biasing mechanism which is configured to bias the drive member into or towards the first position, e.g. when it is in the second position. Thus, the first position may be the standard position of the drive member, particularly when it is not operatively connected to a liquid handling unit. When the liquid handling unit is disconnected from the drive unit, the drive member may be moved back towards or into the first position by the biasing mechanism starting from the second position. The biasing mechanism may comprise a spring, e.g. a compression spring. The spring may be deformed during the movement from the first position into the second position. The biasing mechanism may be arranged in the sealed section of the drive unit housing.

In an embodiment, the mechanism interface between the drive member and the drive mechanism is a releasable interface. In the first position of the drive member relative to the housing and/or the sealing member, the mechanism interface may be released. Thus, in this position, drive member and drive mechanism may be decoupled. Therefore, when the liquid handling unit is disconnected from the drive unit, the drive member, which then may be in the first position, might be exposed to manipulations by the user of the device, e.g. a patient. If the mechanism interface is not established when the liquid handling unit is disconnected from the drive unit the user may manipulate the drive member without the risk of transmitting manipulation forces or torque to the drive mechanism, as the coupling between the drive member and the drive mechanism is released. Thus, the risk of the drive mechanism being damaged by the user is decreased, if the mechanism interface is released when no liquid handling unit is operatively connected to the drive unit. In the second position, the mechanism is expediently established, i.e. the drive mechanism and the drive member are operatively coupled to transfer force and/or torque between one another, expediently from the drive mechanism to the drive member.

In an embodiment, the sealing member is secured to the drive unit housing. The sealing member may be axially and/or rotationally secured to the drive unit housing. Accordingly, axial and/or rotational movement of the sealing member relative to the drive unit housing may be prevented. Consequently, the sealing member may have a securing section, where it is secured to the drive unit housing. The sealing member may furthermore have a sealing section, where it interfaces with the drive member. The sealing section may be radially offset, e.g. inwardly, relative to the securing section. The sealing section and the securing section may overlap axially. The drive member may extend through the sealing section, e.g. through an opening delimited by the sealing section circumferentially.

In an embodiment, the drive member is configured to rotate and/or move axially with respect to the sealing member during operation. For example, when the drive member is in the second position, it may be axially moveable and/or rotatable relative to the sealing member and/or the drive unit housing during operation, for example to move liquid within the liquid handling unit. The sealing member may be engaged with the drive member while the drive member moves during operation. Thus, the sealed interface is expediently also active during operation of the drive unit.

In an embodiment, the sealing member defines a passage, e.g. an opening. The drive member may extend through the passage.

In an embodiment, the section of the drive member which travels along the sealing member during the movement between the first and second section may have a constant outer diameter. At least this section of the drive member may have a cylindrical outer shape.

In an embodiment, the drive member comprises at least two sections with different outer diameters, e.g. a section of greater outer diameter and a section of smaller outer diameter. For example, a first section may have a greater outer diameter than a second section. The sealing member may engage the section of smaller outer diameter of the drive member, e.g. in the first position and/or the second position. This may be true during any axial relative position between sealing member and drive member during operation of the drive unit. The section of greater outer diameter may be arranged outside of the sealed section, e.g. in the first position and/or the second position. The section of the drive member which travels along the sealing member during the movement between the first and second position may have a constant outer diameter. This section may be cylindrical. The section with greater outer diameter may be arranged outside of the sealed section, e.g. in the first and in the second position. Accordingly, the contact area between the sealing member and the drive member may kept small, which may have advantages with respect to frictional losses during operation, when the drive member is in the first position, and/or with respect to the forces required for moving the drive member from the first position into the second position. The section with greater outer diameter may be part of the coupler output portion.

In an embodiment, the sealing member circumferentially engages the drive member. Accordingly, the sealed interface may extend circumferentially, e.g. ring-like, around the drive member.

In an embodiment, the sealing member is an elastic seal. Accordingly, the sealing member may be elastically deformable, in particular at least in a sealing section, which interacts with the drive member or in its entirety. The sealing member may be a rubber seal, for example, or comprise a sealing section of rubber. Elastic seals are particularly suitable to provide tightly sealed interfaces. If the sealing member is elastically deformable, the elastic restoring force which tends to re-establish the non-deformed shape of the sealing member may be used to enhance the sealing efficiency of the sealing member.

In an embodiment, the sealing member is a radial shaft seal. Radial shaft seals are particularly advantageous to provide tightly sealed interfaces, in particular with low frictional losses when the drive member moves relative to the sealing member while the sealed interface is established. The drive member section interacting with the sealing member may be a shaft-shaped section.

In an embodiment, the sealing member engages a radially facing surface of the drive member.

In an embodiment, the sealed interface provided by the sealing member is established in the first position and in the second position. Thus, the sealing may be effective during operation, when the drive unit is operatively coupled to a liquid handling unit and also when no liquid handling unit is provided.

In an embodiment, the sealing member engages the drive member, in particular sealingly, in the first position and/or in the second position. Thus, the sealed interface may be established in both positions.

In an embodiment, the drive unit is configured such that a tightness of the sealed interface is different in the first position and in the second position. Preferably, the sealed interface is tighter in the first position than in the second position. Consequently, when the drive unit is not operatively coupled to the liquid handling unit, i.e. when the drive unit is more exposed to external influences potentially, as the liquid handling unit is not present, the sealed section may be sealed more tightly. When the seal or sealed interface is tighter, a sealing force or contact force between the sealing member and the drive member may be greater than when the sealed interface is less tight. Thus, in the first position, the sealing force or contact force may be greater than in the second position, if the sealed interface is tighter in the first position than in the second position, or vice versa, if the sealed interface in the second position is tighter.

Alternatively, in the first and in the second position, the sealed interface may have the same tightness.

In an embodiment, the drive unit, e.g. the drive member, comprises a transfer member. The transfer member may transfer a force to the sealing member. The force may be a biasing force, e.g. originating from the biasing mechanism such as a spring force. The force may be transferred to the sealing member in the first position, preferably only in the first position, and/or not transferred to the sealing member in the second position. The force may be used to increase the tightness of the seal. Accordingly, the force may be used to increase a sealing force between the sealing member and the drive member or the contact force between the sealing member and the drive member. To increase the sealing force, the direction of the biasing force may be changed. For example, an axially directed biasing force may be converted into a radially, preferably inwardly, directed force, which may increase the force and/or the pressure which the sealing member exerts onto the drive member.

If the transfer member is part of the drive member, it is facilitated that the biasing force of the biasing mechanism can be used not only to move the drive member into the first position but also, when it is in the first position, to increase the sealing or contact force. Thus, in the first position, there may be a remaining bias in the biasing mechanism such that the first position may be defined by the sealing member, as the interface, which secures the sealing member in the drive unit, may counteract the remaining biasing force which still tends to move the drive member beyond the first position. Thus, in the first position, there may be a biasing force which tends to move the drive member away from the second position and/or the first position.

The transfer member may be adjusted and configured to engage an outer surface of the sealing member. The transfer member may transfer an axially directed force to the sealing member. The transfer member may have a sloped surface and/or the sealing member may have a sloped surface. By means of the oblique or sloped surface, the axial force may be converted into a radially, preferably inwardly, directed force to increase the sealing force or contact force between the sealing member and the drive member. Thus, by way of the oblique or sloped surface, an axially directed force may be converted into a radially directed force. Other conversion mechanisms may also be applied as feasible.

In an embodiment, in the first position a first section of the drive member is engaged by the sealing member. In the second position a second section of the drive member is engaged by the sealing member. The first section and the second section may have different outer diameters. The first section may have a greater outer diameter than the second section. Thus, if the sealing member and/or the portion thereof interacting with the drive member is elastically deformable, the elastic restoring force, e.g. in the radial inward direction, may be greater in the first position than in the second position, as the elastic deformation is increased on account of the greater diameter in the first position. In this way, in the first position the tightness may be increased by means of the greater outer diameter of the drive member in the first section. Alternatively, the first section and the second section may have equal outer diameters. This facilitates provision of a sealed interface which has the same tightness in the first position and in the second position.

In an embodiment, the drive mechanism is electrically driven or electrically operated or operable. The drive mechanism is expediently arranged and/or retained in the drive unit housing such as in the sealed section thereof.

In an embodiment, the drive mechanism comprises a motor, in particular, an electric motor. The motor is expediently arranged in the drive unit housing such as in the sealed section thereof.

In an embodiment, the drive unit comprises a power source, e.g. an electrical power source. The power source may be arranged in the drive unit housing. The power source may be operatively, e.g. conductively, connected to the drive mechanism to provide power for moving the drive member relative to the housing and/or the sealing member. For example, the power source is a battery. The battery may be replaceable. The power source is expediently arranged in the sealed section of the drive unit housing.

In an embodiment, the drive unit is reusable. Thus, the drive unit may be used in conjunction with a plurality of liquid handling units. This is particularly efficient, if rather expensive components, such as a drive mechanism, e.g. an electronically controlled drive mechanism, a motor, and/or a power source are arranged in the drive unit housing.

In an embodiment the liquid handling unit comprises a pump mechanism. The pump mechanism may be operable to move liquid from and/or into a reservoir. The reservoir may be comprised by the liquid handling unit. The reservoir may comprise a liquid and/or may be adapted to receive liquid. The pump mechanism may comprise a pump driver. The pump driver may be coupled to the coupler output portion of the drive member of the drive unit, particularly via the coupler input portion of the liquid handling unit. The coupler input portion may be provided on the pump driver or at a part connected to the pump driver, e.g. rigidly connected thereto. When the drive unit and the liquid handling unit are operatively connected, movement of the drive member of the drive unit may be transferred to the pump driver. Movement of the pump driver, e.g. relative to the liquid handling unit housing, may be used to drive a pumping action. If the device is a dispensing device, the pump mechanism may move liquid from the reservoir to an outlet of the device. If the device is a retrieving device, the pump mechanism may move liquid from an inlet of the device into the reservoir. The pump mechanism may comprise a pump chamber. The pump driver or at least a section thereof may be arranged in the pump chamber. Movement of the pump driver relative to the pump chamber may cause movement of liquid in the liquid handling unit.

In an embodiment, the liquid handling unit comprises a liquid guiding conduit. The liquid guiding conduit may have a liquid passage end, e.g. an inlet or an outlet. The inlet or the outlet may form the inlet or the outlet of the device. The liquid guiding conduit may be fluidly connected to the reservoir. The pump chamber, within which a pumping portion of the pump driver may be moveably arranged, is preferably arranged in the liquid guiding conduit, particularly between the liquid passage end and the reservoir as seen along the flow path between the reservoir and the liquid passage end. Accordingly, the pump driver may govern the movement of liquid along the liquid guiding conduit, e.g. for dispensing liquid from the reservoir through the liquid passage and/or for retrieving liquid from an object, e.g. the body of a mammal, through the liquid passage end.

In an embodiment, the liquid handling unit is releasably connected to the drive unit, e.g. via a snap fit or another suitable connection. Thus, the liquid handling unit may be detached from the drive unit and disposed of and the drive unit may be reused in conjunction with a different liquid handling unit. Although the liquid handling unit comprises the pump mechanism and the reservoir, it may nevertheless be disposed of after use in the proposed concepts as the pump mechanism may be comparatively easy and cost effective to manufacture such that the costs of the liquid handling unit with an integrated pump mechanism are still tolerable. Moreover, if the liquid handling unit is disposable, the pump mechanism and/or the associated conduit can be disposed as well and the risk that the pump mechanism and the conduit are contaminated is reduced as opposed to a device where the pump mechanism were reused.

In an embodiment, the liquid handling unit comprises a liquid handling unit housing. The reservoir and/or the pump mechanism, in particular the pump driver, may be arranged and/or retained in the liquid handling unit housing. The liquid guiding conduit may be arranged or defined in the liquid handling unit housing.

In an embodiment, in the device, the liquid handling or guiding functionality is restricted to the liquid handling unit and the drive functionality, preferably the entire drive functionality, for moving liquid within the liquid handling unit is provided by the drive unit. Contact between an element, preferably all elements, of the drive unit and the liquid may be prevented during operation of the device.

In an embodiment, the device comprises a mounting surface. The mounting surface may be configured for mounting the device to a body of a mammal, e.g. a human, for example a patient, which should be treated by a drug retained in the reservoir. The device may be fixed to the skin of the mammal via the mounting surface. The mounting surface may be a surface of the liquid handling unit or a surface of the drive unit. If the mounting surface is a surface of the liquid handling unit a fixing means to secure the device to the body may be exchanged together with the liquid handling unit. If the mounting surface is provided on the drive unit, the liquid handling unit may be exchanged, while the drive unit is still mounted on the body, e.g. at a pre-defined location, which may have been selected by a physician for example.

In an embodiment, the mounting surface is provided with an adhesive. Via the adhesive, the device may be secured to the body.

In an embodiment, the device is designed to stay connected to the body for a longer period of time, e.g. days or weeks.

In an embodiment, the device is a patch pump. Consequently, the device comprises a pump mechanism and can be applied like a patch on an object or a surface such as on a body of a mammal.

In an embodiment, the device is a drug delivery device. A liquid drug may be retained in the reservoir. Thus, the liquid drug may be dispensed from the reservoir and from the device by means of the drive unit.

In an embodiment, the device comprises an actuator, which, when operated, triggers an operation of the device, e.g. a delivery operation to dispense liquid, such as a dose delivery operation, e.g. for dispensing a dose, i.e. a selected sub-quantity of the drug contained in the reservoir, of drug from the device. The actuator may be user operable. The actuator may be provided on the drive unit. For example, the actuator may be a button, which can be touched by a user, e.g. in order to trigger a dispensing action for dispensing liquid from the reservoir. Of course, with respect to the exterior, the actuator may be sealed, such that the seal of the sealed section of the interior of the housing is not jeopardized.

In an embodiment, the end passage of the liquid handling unit is provided by a needle or needle tip and/or a connector, which is either provided to be, e.g. releasably or permanently, connected with a needle, such as a threaded connector, or a tube, such as a luer connector, which connects the liquid guiding conduit to a tubing. If no needle connector is provided, the needle may be integrated into the liquid handling unit as an integral part. The needle may then be disposed of together with the liquid handling unit.

BRIEF DESCRIPTION OF THE FIGURES

Further features, advantages and expediencies of the present disclosure will become apparent from the following description of the exemplary embodiments in conjunction with the drawings.

Identical elements, elements of the same kind and identically acting elements may be provided with the same reference numerals in the figures.

Figure 9:
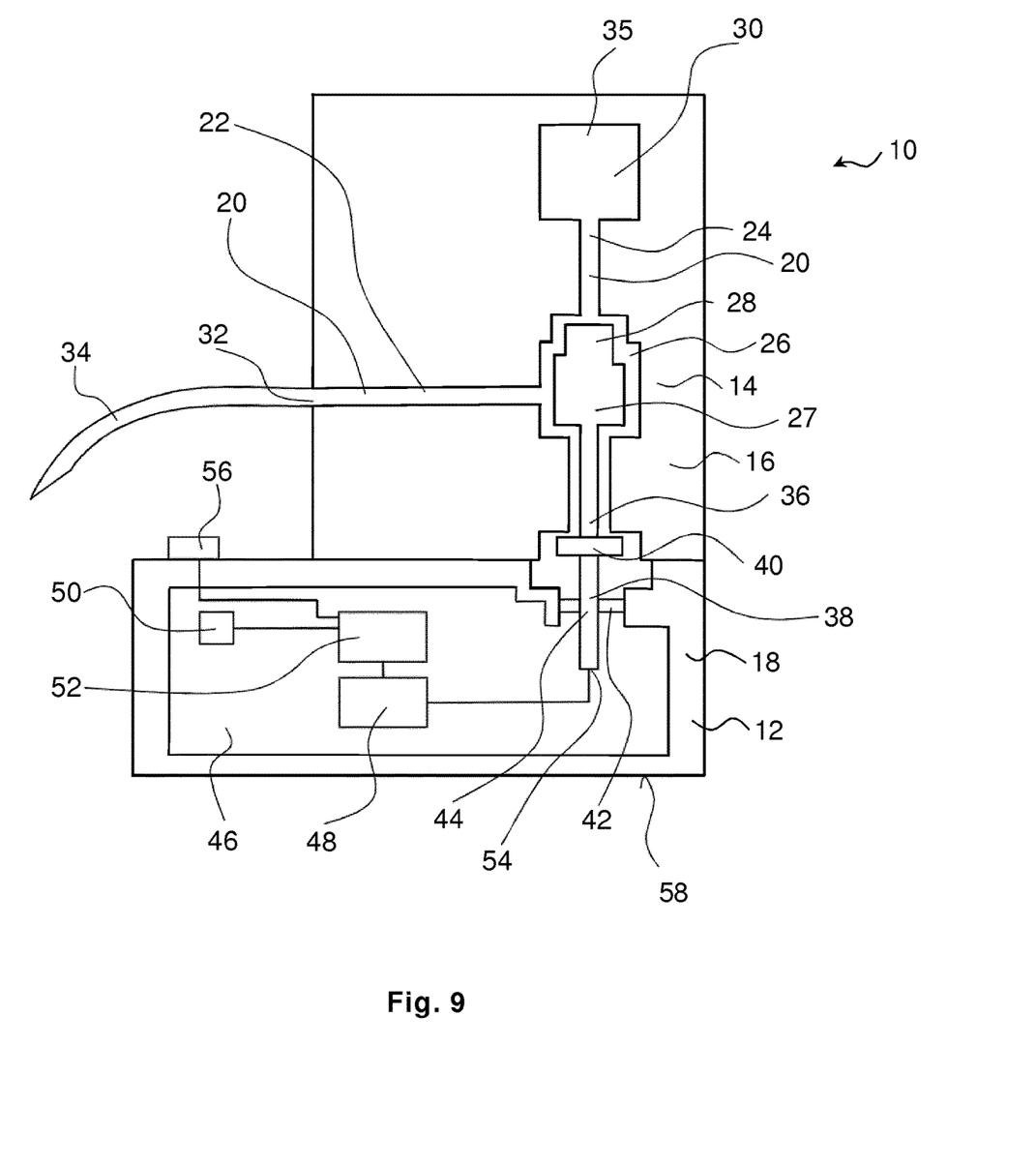
FIG. 9 schematically illustrates an exemplary embodiment of a liquid handling device which may comprise the drive unit of one of the embodiments illustrated by way of FIGS. 1 through 4.

FIG. 9 shows an exemplary embodiment of a liquid handling device, particularly a medical device. The depicted embodiment is a drug delivery device 10, which is designed to deliver a drug or a medicament. Of course, the disclosed concepts can be applied to other liquid handling or medical devices as well, be it liquid dispensing devices or liquid retrieving devices.

DETAILED DESCRIPTION

The drug delivery device 10 comprises a drive unit 12 and a liquid handling unit 14. The drive unit 12 and the liquid handling unit 14 are releasably attached or secured to one another. The liquid handling unit 14 may be a disposable unit, which may be replaced with a new one, for example because the drug or medicament in the liquid handling unit has been used up. The drive unit 12 is expediently a reusable unit, which can be used together with several liquid handling units. The releasable connection may be effected by a snap fit connection, a press fit connection, a Velcro connection, a releasable adhesive connection or the like. The specific connection means between the drive unit 12 and the liquid handling unit 14 is not explicitly illustrated. The liquid handling unit 14 comprises a liquid unit housing 16. The drive unit 12 comprises a drive unit housing 18. Mating connection means, not explicitly illustrated, may be provided on end faces of the liquid handling unit housing 16 and the drive unit housing 18, which face one another, and, when in mechanical cooperation, attach the liquid handling housing 16 releasably to the drive unit housing 18.

The liquid handling unit 14 comprises a liquid guiding conduit 20. Along the liquid guiding conduit 20, liquid may be guided in the liquid handling unit during operation of the device 10. The conduit 20 may be defined in the housing, e.g. by providing a channel structure in the housing as depicted, or, alternatively, by a tube system arranged in the housing, if applicable in combination with a channel structure. The conduit 20 has at least two different sections, a first section 22 and a second section 24. In the flow path between the two sections 22 and 24 a pump chamber 26 is arranged, which is in fluid communication with the section 22 and the section 24 of the conduit 20. The sections 22 and 24 preferably extend away from different openings which provide access to the pump chamber. Within the pump chamber 26, a pump portion 27, e.g. a pump head, of a pump driver 28 may be arranged. The pump driver 28 is movable relative to the pump chamber 26 to move fluid along the conduit e.g. from the first section 22 into the second section 24 and/or vice versa. The pump driver 28 may, for example, be rotatable in the pump chamber 26. The pump driver 28 may be a rotor. The walls of the chamber may serve as a stator of a rotationally operating pump. The stator may cooperate with the rotor to provide a pumping action when the pump driver 28 is rotated relative to the pump chamber and/or the liquid handling unit housing.

The liquid handling unit 14 further comprises a reservoir 30. The section 24 is in fluid communication with the reservoir 30. Particularly, the section 24 is arranged in the flow path between the reservoir 30 and the pump chamber 26. The section 22 is in fluid communication with a liquid passage end 32 or open end of the conduit 20.

In FIG. 9 the end of the conduit 20 is highlighted by reference 32. The section 22 is arranged in the flow path between the pump chamber 26 and the end 32. The end 32 may for example be formed by an opening in the liquid handling unit housing 16. The end 32 may either be provided with a connector (not explicitly shown) such as a tube connector for fluidly connecting a tube to the conduit 20 of the liquid handling unit, e.g. a Luer connector, and/or a needle connector for, e.g. releasably, connecting a needle unit to the housing and fluidly to the conduit 20. Alternatively, a needle 34 may be provided in the liquid handling unit 14 in fluid communication with the conduit, in particular section 22 thereof, as depicted. The needle 34 may form an integral part of the liquid handling unit, i.e. it is not designed to be detached from the liquid handling unit.

Through the end 32 liquid may be dispensed from the liquid handling unit housing 16. If a needle is provided as is depicted by needle 34, the needle may penetrate the skin of a user, e.g. a human patient. Through the needle 34, liquid, e.g. a drug, may be dispensed into the body of a mammal or retrieved therefrom, e.g. blood, when the device is operated.

The reservoir 30, in case of a drug delivery device as liquid handling device, expediently comprises a liquid drug 35 or a medicament.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The reservoir 30 may be defined by a reservoir chamber within the liquid handling unit housing 16 and delimited by the walls of the housing, where the reservoir chamber is filled with liquid, as depicted, or, alternatively, may be a separate component, such as a cartridge or a bag or another, e.g. prefilled, container, which is fluidly connected to the conduit 20 during manufacture of the liquid handling unit 14.

The pump driver 28 is expediently permanently retained in the liquid handling unit housing 16. Therefore, if the liquid handling unit 14 is disposed, the pump driver is disposed as well. Thus, all parts of the device 10, which contact, move, and guide liquid during operation of the device may be disposed, in particular together with the liquid handling unit 14.

The liquid handling unit 14 furthermore comprises a coupler input portion or input coupler 36. The coupler input portion 36 may be provided to establish a mechanical interface to the drive unit. The coupler input portion may be operatively connected to the pump driver 28. The coupler input portion may be formed by a portion of the pump driver or another member of the liquid handling unit, which is operatively connected to the pump driver, e.g. rotationally and/or axially locked to the pump driver 28. Via the coupler input portion force or torque may be transferred from the drive unit 12 to the pump driver 28 in order to move the pump driver to provide a pumping action.

The drive unit 12 comprises a drive member 38. The drive member 38 is moveably retained in the drive unit housing 18. The drive unit 12 is configured to move the drive member 38 in order to transfer forces or torque to the pump driver 28. The drive member comprises a coupler output portion 40. As depicted in FIG. 9, the coupler output portion 40 of the drive member is operatively and preferably mechanically coupled to the coupler input portion 36 of the liquid handling unit 14. For example, the coupler output portion 40 and the coupler input portion 36 may be coupled by a splined coupling so that, when coupled, they are rotationally interlocked and rotation of the drive member 38 is transferred to the pump driver 28 via the coupler input portion 36 to rotate the pump driver relative to the liquid handling unit housing 16 in the pump chamber 26. Alternatively or additionally, if the pump driver 28 performs axial movement, e.g. only axial movement or axial and rotational movement, relative to the pump chamber 26, the drive member 38 may move axially relative to the drive unit housing 12, e.g. only axially or axially and rotationally as the case may be.

As depicted in FIG. 9 schematically, the drive unit 12 comprises a sealing member 42. The sealing member 42 is in sealing engagement with the drive member 38, e.g. it abuts the drive member 38. The drive member 38 extends through the sealing member. A radially facing surface of the drive member is contacted by the sealing member 42 to establish the sealed interface. The sealed interface may be provided along the entire circumference of the drive member 38.

The drive member 38 may have portions of different outer diameters. For example, the portion 44 of the drive member which is arranged to abut the sealing member 42 may have a radial dimension, e.g. an outer diameter, which is less than the one of the coupler output portion 40 of the drive member 38. The portion 44 may have a cylindrical external surface. Portion 44 may be formed shaft-like.

The sealing member 42 may delimit or define a sealed interior 46 or sealed section of the interior of the drive unit housing 18. As the interface to the exterior is sealed via the sealing member 42, environmental influences like moisture, water and/or durst are prevented from reaching the interior of the drive unit housing and, consequently, more sensible components of the drive unit may be arranged in this section.

As the portion 44 has a reduced diameter, frictional losses during rotation and/or axial movement of the drive member 38 along the sealing member 42 may be kept reasonable, on account of a contact surface between the drive member and the sealing member which is smaller as compared to the outer surface of the coupler output portion 38, for example. The outer diameter of portion 44 may be less than or equal to 0.5D, 0.3D, 0.2D, 0.15D, or 0.1D, where D is the outer diameter of another portion of the drive member, e.g. a portion outside of the sealed section such as the coupler output portion 40. D may be the maximum outer diameter of the drive member 38 and/or the coupler output portion 40.

Within the sealed interior section 46 of the drive unit housing 18, one or more other elements of the drive unit may be arranged. The elements in the interior may include: a drive mechanism, e.g. comprising a motor 48, a power source 50, such as a battery, and/or a control unit 52, such as an electronic control unit.

The drive member 38 may extend through the sealing member 42 and thus provide an exterior interface for the drive unit while the other elements are protected in the sealed interior 46. The motor 48 may be an electrically operated motor. The power source 50 may provide the electrical power to operate the motor 48 to drive movement of the drive member 38 relative to the drive unit housing 18 and/or the sealing member 42. The control unit 52 may be operatively and/or conductively connected to the power source 50 and/or the motor 48 to control operation of these elements and/or control the power supply from the power source to the motor.

Between the drive mechanism and the drive member a mechanism interface 54 may be provided. Via the mechanism interface, which is preferably established in the sealed interior section 46, the driving force or torque may be transferred from the drive mechanism to the drive member 38, e.g. via a moving shaft, e.g a rotating shaft, which is coupled to the drive member in the sealed interior 46 to generate an, e.g. rotational, movement of the drive member 38 during operation of the device 10. The movement of the drive member 38 may be transferred to the pump driver 28 via the coupling established between the coupler output portion 40 of the drive unit 12 and the coupler input portion 36 of the liquid handling unit 14.

The drive unit 12 comprises an actuator 56, e.g. a button. The actuator may be actuatable by a user, for example to trigger a dispensing action for delivering drug retained in the reservoir 30 from the device. A user interface of the actuator may be accessible from the exterior of the drive unit housing. The actuator may be operatively connected to the control unit 52. Actuation of the actuator may cause the control unit 52 to operate the drive mechanism such that the pump driver 28 can move within the pump chamber 26. If there is a path of fluid communication along the actuator to the interior of the drive unit housing, this path is expediently sealed such that the sealing of the sealed interior is maintained.

The depicted device 10 may be a patch pump. A patch pump is a device, which can be attached to the skin of a user and stays there for an extended period of time, e.g. for days or weeks. If the user recognizes that a delivery of medicament is required, he may, preferably manually, actuate the dispensing action, e.g. via the actuator. As opposed to closed-loop systems, which may be used as artificial pancreas for delivering insulin, patch pumps tend to be less sophisticated, as no sensors are typically needed which measure the glucose level, for example. However, patch pumps still may be useful to provide medicament to the patient by means of self-administration.

A fixing surface 58, which is provided to be attached to the user, may be provided at the drive unit 12, for example on that surface of the drive unit 12, which is opposite of the liquid handling unit 14 as depicted. Alternatively, the fixing surface may be provided on the liquid handling unit, such as on that surface, which faces away from the drive unit (not shown). Moreover, a portion of the fixing surface may be provided on each of the drive unit 12 and the liquid handling unit 14. Therefore, the fixing surface may be provided at various places of the device. However, only one region is highlighted in FIG. 5, i.e. the one on the drive unit, where the fixing surface 58 is shown. The fixing surface may be provided with an adhesive. The same holds for the remaining fixing surfaces mentioned above, such that the device 10 may be adhesively attached to the skin of a user. If the device 10 is worn by the user at the user's body for an extended period of time, it is particularly expedient to seal the interior of the drive unit, for example to avoid that moisture, such as when the user takes a shower, dust or other dirt can enter the interior of the drive unit housing 18.

The sealing member 42 provides the sealed interface with the drive member 38 when the liquid handling unit 14 is attached to the drive unit 12 and also when it is detached. The drive member is in different axial position relative to the sealing member 42 when the liquid handling unit is attached and when it is detached.

In the following, several embodiments, which employ a sealing member 42, are explained based on sectional views of portions of the device 10 shown in FIG. 9. One embodiment is discussed in conjunction with FIGS. 1 and 2, another one in conjunction with FIGS. 3 and 4, still another one in conjunction with FIGS. 5, 5A, 6, and 6A and yet another one in conjunction with FIGS. 7 and 8.

Figure 1:
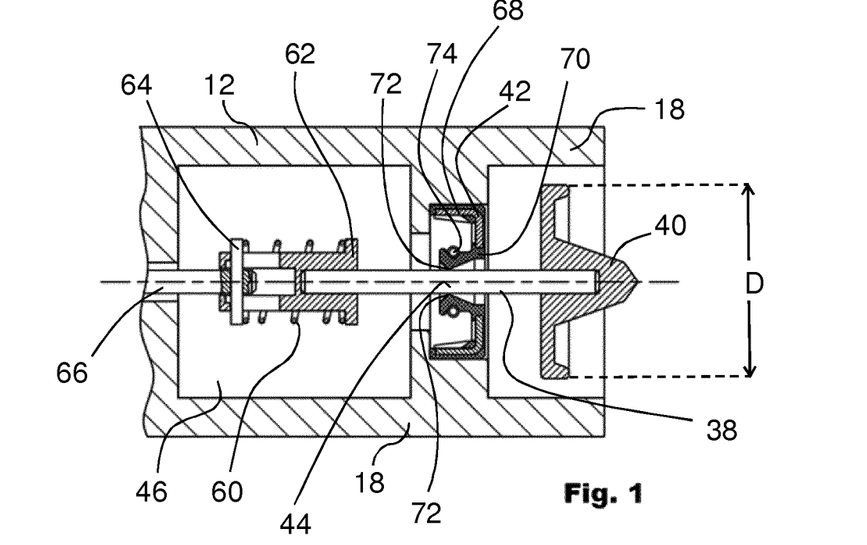
FIGS. 1 and 2 each show a schematic sectional view of a portion of one embodiment of a drive unit in different states, i.e. not coupled to a liquid handling unit in FIG. 1 and coupled to a liquid handling unit in FIG. 2.
Figure 2:
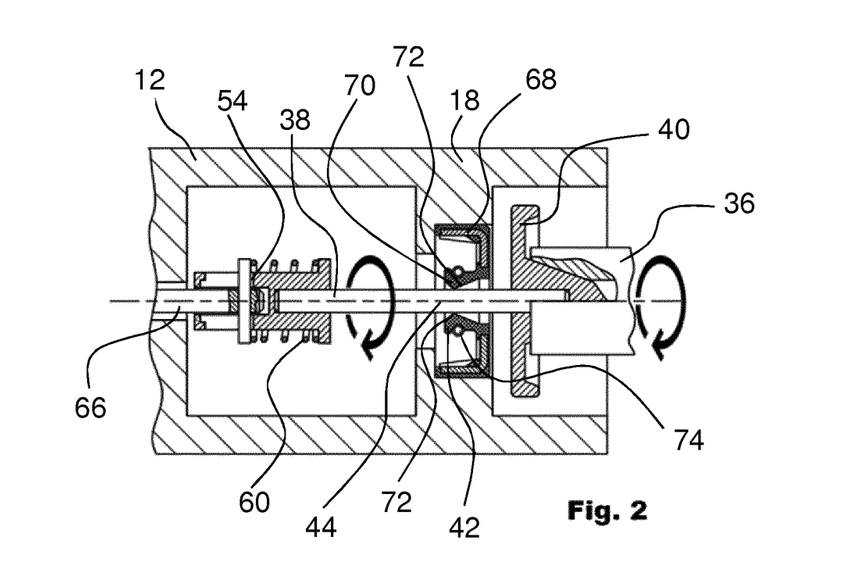

In FIG. 2, there is shown a section of the device as depicted in FIG. 9. In particular, the section around the sealing member 42 is shown. FIG. 1 shows the section of the drive unit 12 of FIG. 9, when no liquid handling unit 14 is connected operatively to the drive unit 12.

As can be seen, the drive member 38 comprises a drive member interface portion 62 or member. The drive mechanism comprises a drive mechanism interface member 64. The drive mechanism interface member is coupled to a drive mechanism member 66, e.g. a shaft, which may be coupled to the motor and be driveable by the motor. At least in the position depicted in FIG. 2, when the liquid handling unit is attached, i.e. in the second position of the drive member, the mechanism interface 54 is established. The mechanism interface couples the drive member to the drive mechanism or motor which is not explicitly shown in the figure. When the mechanism interface 54 is established, the drive member and the interface member may be rotationally locked to one another, e.g. by mating teeth of the interface portion 62 and the interface member 64 engaging. Thus, in the second position depicted in FIG. 2, the drive member is operatively connected to the interface member 64 to transfer rotational movement from the drive mechanism to the drive member and the coupler output portion 40 thereof, which causes rotation of the coupler input portion 36 of the liquid handling unit 14 and, accordingly, of the pump driver as is indicated by the arrows. In the position in FIG. 1, i.e. the first position, the interface member 66 may be operatively disconnected from the drive member. Alternatively, there may be an operative connection, i.e. the mechanism interface may be established also in the first position of the drive member 38 relative to the sealing member (see FIG. 1). However, if the drive member and the interface member 66 are operatively disconnected in the first position, i.e. the mechanism interface is not established, a manipulation of the coupler output portion 40 is not transferred to the elements of the drive mechanism in the sealed interior 46. This may be advantageous.

As is apparent from the figures, preferably within the sealed section 46 of the interior of the drive unit housing 18, a biasing mechanism is provided, which comprises a spring 60, e.g. a compression spring. The biasing mechanism biases the coupler outer portion 40 and/or the drive member 38 to the position in FIG. 1 (first position) when the drive member is in the position depicted in FIG. 2 (second position). The spring 60 may be retained between the drive member interface portion 62 and the drive mechanism interface member 64. In the position shown in FIG. 2, the coupler input portion 36 is operatively connected to the coupler output portion 40. That is to say, the liquid handling unit 14 has been connected to the drive unit 12 operatively and preferably mechanically. In the second position, the drive member 38 has been displaced relative to the sealing member 42, such that the spring 60 is compressed and maintains the coupler output member 40 and the coupler input member 36 in engagement.

The sealing member 42 is axially and preferably rotationally secured relative to the drive unit housing 18. The sealing member 42 may have a fixing portion 68. In the fixing portion 68, the sealing member 42 may be secured to the drive unit housing 18. The sealing member 42 may have a guiding portion or sealing portion 70. The portion 70 may extend sleeve-like along the drive member 38. At least in the sealing portion 70 the sealing member 42 is, preferably elastically, deformable. At least the sealing portion 70 or the entire sealing member 42 may be made of rubber. The fixing portion 68 may be less easily deformable than the sealing portion, e.g. more rigid or stiff. The fixing portion 68 may be structurally reinforced, e.g. to provide appropriate rigidity, and/or be resilient, e.g. it may comprise a spring member, for example of metal. A radially resilient fixing portion may assist in securing the sealing member 42 to the drive unit housing 18, e.g. by clamping the sealing member to the drive unit housing such as by exerting a radial outward force which is reacted by an inner wall of the housing. The sealing portion 70 may be radially inwardly offset from the fixing portion 68. The sealing portion 70 and the fixing portion 68 may be axially aligned. A radially outwardly facing surface of the sealing portion 70 may be arranged radially offset from a radially inwardly facing surface of the fixing portion 68. The radially outwardly facing surface of the sealing portion 70 may axially overlap with and/or face the radially inwardly facing surface of the fixing portion 68. The sealing member 42 comprises a sealing surface or sealing lip. The sealing surface or lip 72 may be arranged in the interior of the sealing portion. The sealing surface or lip 72 may protrude radially inwardly into a hollow defined by the sealing portion 70. The sealing surface or lip 72 may have a pointed and/or radially inwardly protruding end. The sealing surface or lip 72 may extend circumferentially around the drive member 38. The sealing portion 70 may have muffle-like or sleeve-like shape. A radial free end of the surface or lip 72 may sealingly engage the drive member 38.

The sealing portion 70 may be radially reinforced. For this purpose, a reinforcing member 74, e.g. a rigid ring, may extend around an outer surface of the sealing portion 68, in particular in the same axial region where the sealing surface or lip 72 is arranged. The reinforcement member may stabilize the sealing portion 70 against extensive radial deflection. Thus, the sealing force may be increased. The sealing surface 72, however, is preferably still radially deformable.

By way of the sealing member 42, dirt or moisture is prevented from entering the sealed interior 46 of the drive unit 12 and, at the same time, frictional losses caused by the sealing member can be kept at a minimum.

Figure 3:
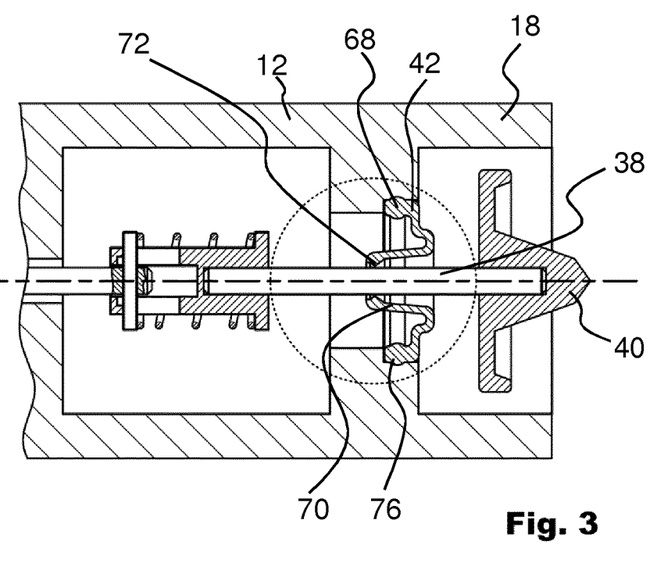
FIGS. 3 and 4 each show a schematic sectional view of a portion of one embodiment of a drive unit in different states, i.e. not coupled to a liquid handling unit in FIG. 3 and coupled to a liquid handling unit in FIG. 4.
Figure 4:
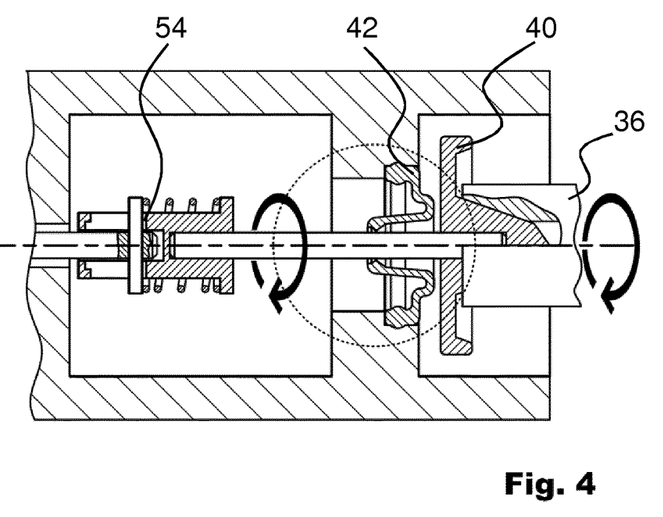

In the following, several further embodiments of the drive unit 12 with sealing member 42 are discussed. The discussion in each case focuses on the differences to the other embodiments, e.g. the one discussed above. However, even though not explicitly described, features described before also apply to the following embodiments unless it is apparent that they cannot apply. The embodiment depicted in FIGS. 3 and 4 is very similar to the one depicted in FIGS. 1 and 2. The sealing member 42, however, is different. As depicted, the sealing member 42 is also a radial shaft seal. The sealing member 42 comprises a fixing portion 68 and a ceiling portion 70 as well. However, reinforcements or spring structures may not be included in the sealing member 42. Rather, the sealing member 42 may be a unitary body of elastic material, e.g. of rubber. The fixing portion may fix the sealing member to the drive unit housing 18 in a force-fit engagement, e.g. by way of a snap-fit, where a snap interface is formed between the drive unit housing and the sealing member. For doing so, for example a ring-like circumferential protrusion 76 of the sealing member may engage a correspondingly shaped ring-like recess in the drive unit housing. The protrusion 76 may be provided on the sealing member and the recess on the housing or vice versa. The sealing member 42 is axially secured to the housing. The sealing member 42 may comprise a circumferentially disposed region of increased radial wall thickness which increases the radial stability of the sealing member. The protrusion 76 may be formed by an outer surface of this region. An inwardly pointing protrusion may also be formed which is arranged to face the sealing section 70. The inwardly pointing protrusion and the protrusion 76 together may define a ring-like structure.

Figure 5:
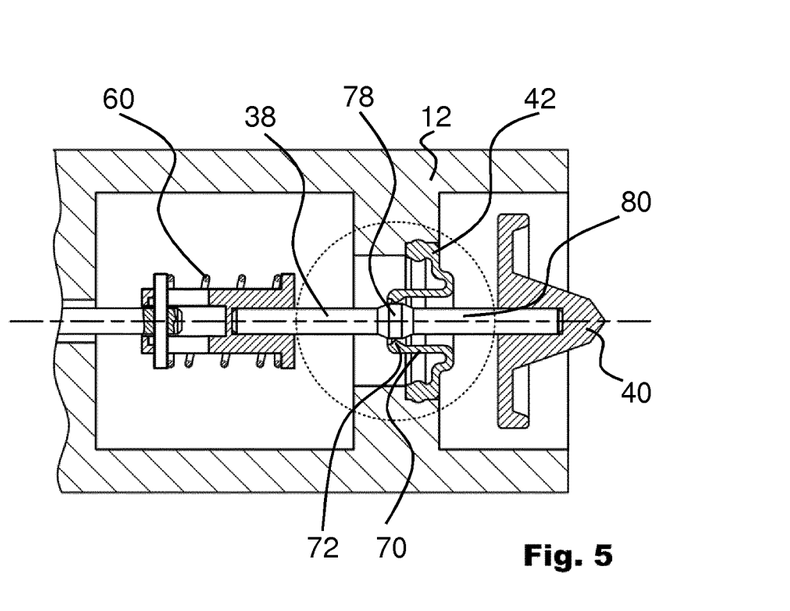
FIGS. 5 and 6 each show a schematic sectional view of a portion of one embodiment of a drive unit in different states, i.e. not coupled to a liquid handling unit in FIG. 5 and coupled to a liquid handling unit in FIG. 6.
Figure 5A:
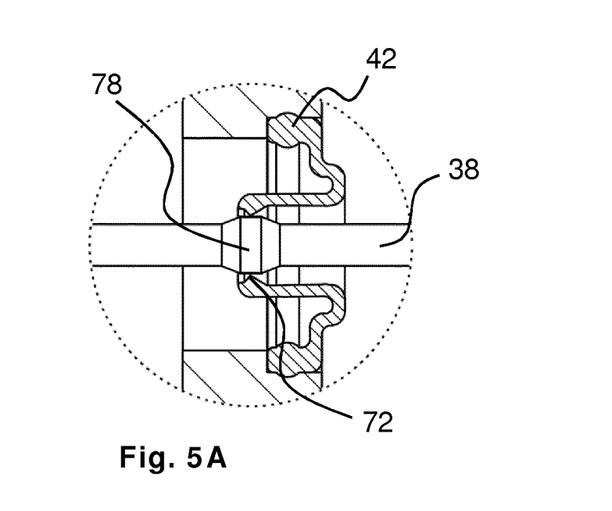
FIG. 5A shows a region of FIG. 5 and FIG. 6A the same region but in the state depicted in FIG. 6.
Figure 6:
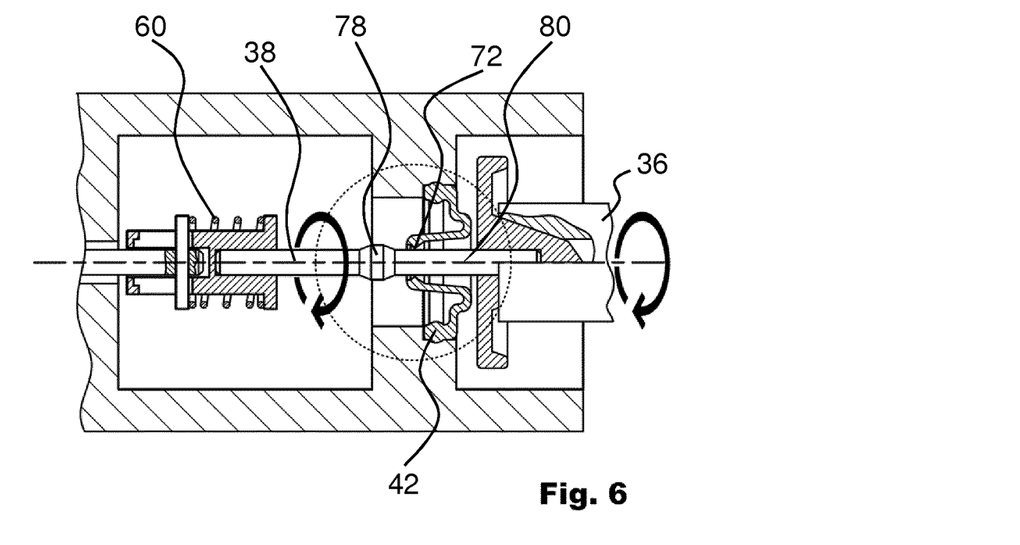
Figure 6A:
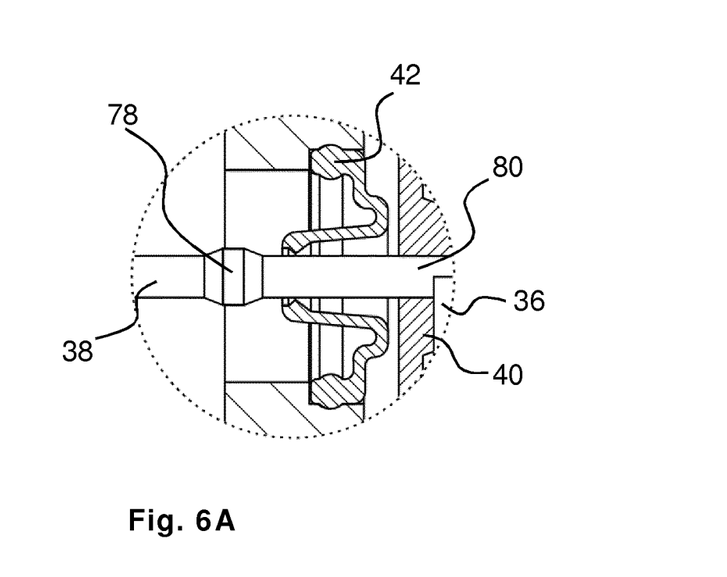

The embodiment shown in FIGS. 5, 5A, 6, and 6A largely corresponds to the one shown in FIGS. 3 and 4. However, in this embodiment, it is ensured that in the first position, depicted in FIG. 5, when the liquid handling unit is not coupled to the drive unit 12, the tightness of the sealed interface between the sealing member 42 and the drive member 38 is increased as compared to FIG. 3. For increasing the tightness of the sealed interface, it is ensured that, in the first position which is depicted in FIG. 5, the sealing surface 72 is radially outwardly displaced relative to the position of the sealing surface 72 in the second position depicted in FIG. 6. As the sealing surface 72, the sealing portion 70 or the entire sealing member is elastically deformable or resilient, in FIG. 5 the restoring force which tends to restore the undefined shape the sealing portion 70 is increased as compared to the FIG. 6 situation where the liquid handling unit 14 is coupled to the drive unit 12.

The drive member 38 comprises two different sections, a first section 78 and a second section 80. In the first position, the sealing member 42 engages the first section 78 and in the second position the sealing member engages the second section 80. The sections 78 and 80 have different outer diameters. Particularly, the outer diameter of the first section 78 is greater than the one of the second section 80. Thus, the elastic deformation in the first position is greater and results in correspondingly increased elastic restoring force, which acts radially inwardly and increases the tightness of the seal in the first position over the one in the second position, where the diameter is smaller. Between the first section 78 and the second section 80, a sloped surface may be arranged to allow for a smooth radial displacement of the sealing surface 72 and the elastic deformation of the sealing portion 70 of the sealing member 42. In the second position, the sealing force is still present but smaller than in the first position such that the movement to drive operation in the liquid handling unit is not hindered significantly while still maintaining a sealed interface. In the second position, the drive member 38 has been displaced relative to the sealing member 42 such that the second section 80 is brought into engagement with the sealing member 42.

Figure 7:
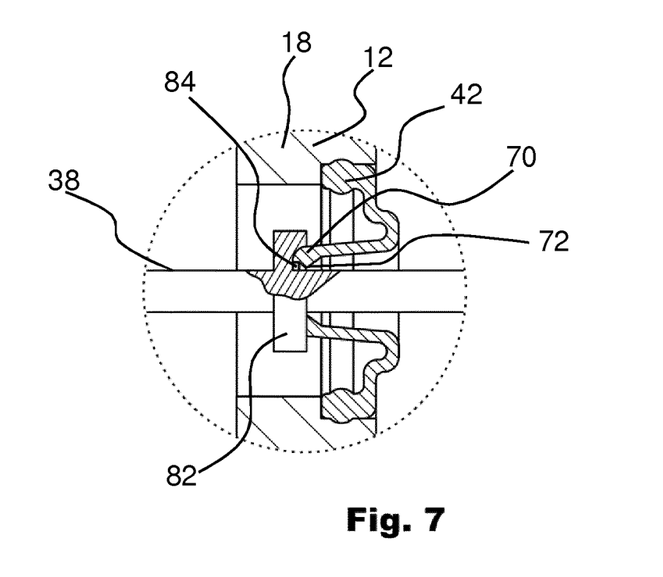
FIGS. 7 and 8 each show a schematic sectional view of a portion of one embodiment of a drive unit in different states, i.e. not coupled to a liquid handling unit in FIG. 7 and coupled to a liquid handling unit in FIG. 8.
Figure 8:
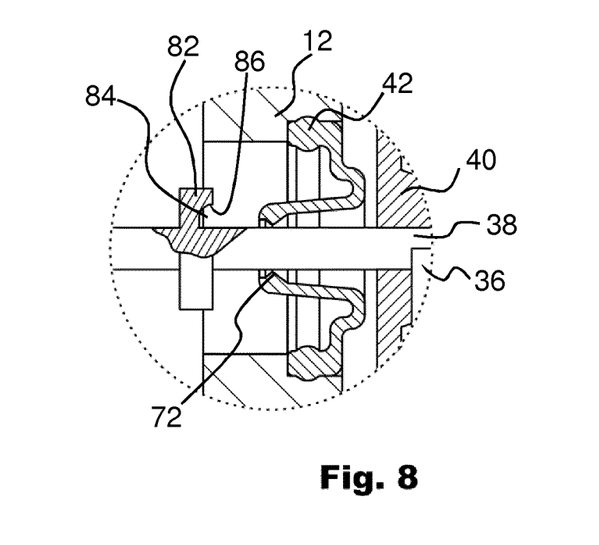

The embodiment depicted in FIGS. 7 and 8 is also an embodiment, where the tightness of the sealed interface in the first position of the drive member 38 is increased as compared to the second position. However, the solution is different as compared to the one described previously. The drive member comprises a transfer member 82. The transfer member 82 may be a protrusion on the drive member. The transfer member 82 may extend circumferentially around the drive member or not. The transfer member 82 may have a, e.g. circumferential, recess 84 which is configured to receive a section of the sealing member and/or to radially inwardly displace the sealing surface 72 and to maintain the sealing surface in the displaced position if the drive member 38 is in the first position relative to the sealing member 42. The radial inward displacement may be effected by an oblique or curved surface on one of the sealing member and the transfer member which interacts with a corresponding surface of the other element when the drive member moves relative to the sealing member from the second position into the first position. As depicted, the recess 84 may have a sloped or curved surface 86, which interacts with a corresponding surface of the sealing portion 70. Due to the mechanical cooperation between the transfer member 82 and the sealing member 42, a force can be transferred to the sealing member 42 via the drive member. This force may be a residual biasing force still present in the spring 60 in the first position. The force may be used to radially inwardly displace the sealing surface 72 on account of the public surface of the transfer member. The force transferred by the drive member to the sealing member is expediently an axially directed force. The axially directed force may be converted into a radial inwardly directed force by the surface 86, which increases the tightness of the seal. As the transfer member stays in contact with the sealing member in the first position, a radial outward movement of the sealing surface is prevented. The remaining axially directed force, e.g. the spring force, may be reacted by the axial fixation of the sealing member to the drive unit housing 18, accordingly.

Therefore, in the first position (FIG. 7), the sealed interface is tighter as opposed to the second position (FIG. 8), where the transfer member 82 is not in mechanical cooperation with the sealing member 42.

In the present disclosure, the drive unit, the liquid handling unit and/or the medical device, in particular an interior of the respective entity, may be sealed against moisture, water, water jets, and/or dust. The respective seal may be effected by the sealing member 42 and/or one or more additional sealing members, e.g. one which seals the actuator and/or one which seals a power source replacement closure which can be opened to replace the power source. For example, the respective entity—drive unit, liquid handling unit, or medical device where the drive unit and the liquid handling unit are assembled to one another—may have a water ingress protection, e.g. as defined in EN 60529. For example, when the liquid handling unit is connected to the drive unit, the assembly preferably provides water ingress protection of class IPX5 and/or IPX8 according to EN 60529. The test conditions for class IPX8 are defined as: submerged to 3.6 m for at least 1 h and submerged to 1.0 m for at least 2 h. The reusable drive unit individually, i.e. when the liquid handling unit is not connected to the drive unit or when the drive member is in the first position, preferably provides water ingress protection of class IPX5 and/or IPX7 according to EN 60529.

The scope of the appended claims shall not be limited by the description of the exemplary embodiments presented above.

REFERENCE NUMERALS 10 drug delivery device
12 drive unit
14 liquid handling unit
16 liquid handling unit housing
18 drive unit housing
20 conduit
22 section
24 section
26 pump chamber
27 pump portion
28 pump driver
30 reservoir
32 end
34 needle
35 drug
36 coupler input portion
38 drive member
40 coupler output portion
42 sealing member
44 portion
46 sealed interior
48 motor
50 power source
52 control unit
54 mechanism interface
56 actuator
58 surface
60 spring
62 drive member interface portion
64 drive mechanism interface member
66 drive mechanism member
68 fixing portion
70 sealing portion
72 sealing surface
74 reinforcement member
76 protrusion
78 drive member section
80 drive member section
82 transfer member
84 recess
86 surface

The invention claimed is:

1. A drive unit for a medical device, comprising:
   a drive unit housing;
   a drive member retained in the drive unit housing and movable relative to the drive unit housing to drive an operation of the medical device, the drive member comprising a coupler output portion configured to be operatively connected to a liquid handling unit;
   a drive mechanism retained in the drive unit housing, wherein the drive mechanism is coupleable to the drive member via a mechanism interface and configured to transfer a driving force or torque to the drive member; and
   a sealing member configured to establish a sealed interface with the drive member, the drive member being movable relative to the sealing member from a first position to a second position, and a tightness of the sealed interface being different in the first position than in the second position, wherein the sealed interface defines a sealed section of an interior of the drive unit housing,
   wherein the mechanism interface is arranged within the sealed section and the coupler output portion is arranged outside of the sealed section.

2. The drive unit of claim 1, wherein the drive unit is configured such that the tightness of the sealed interface is tighter in the first position than in the second position.

3. The drive unit of claim 1, wherein the sealing member is a radial shaft seal.

4. The drive unit of claim 1, wherein the drive mechanism is an electrically operated drive mechanism comprising an electric motor and an electrical power source arranged in the drive unit housing.

5. The drive unit of claim 1, wherein the drive mechanism is coupled to the drive member.

6. The drive unit of claim 1, wherein the drive member is axially movable relative to the sealing member from the first position to the second position, and the drive unit comprises a biasing mechanism configured to bias the drive member into the first position.

7. The drive unit of claim 6, wherein the sealing member is configured to sealingly engage the drive member in the first position and in the second position.

8. The drive unit of claim 7, wherein a first section of the drive member which is engaged by the sealing member in the first position has a greater outer diameter than a second section of the drive member which is engaged by the sealing member in the second position.

9. The drive unit of claim 8, wherein the drive member comprises a transfer member configured to transfer a biasing force from the biasing mechanism to the sealing member in the first position and the biasing force is used to increase a sealing force between the sealing member and the drive member.

10. A medical device, comprising:
a liquid handling unit comprising (i) a reservoir adapted to receive a liquid and (ii) a pump mechanism operable to move the liquid from the reservoir; and
a drive unit comprising
a drive unit housing;
a drive member retained in the drive unit housing and movable relative to the drive unit housing to drive an operation of the medical device, the drive member comprising a coupler output portion configured to be operatively connected to the liquid handling unit;
a drive mechanism retained in the drive unit housing, wherein the drive mechanism is coupleable to the drive member via a mechanism interface and configured to transfer a driving force or torque to the drive member; and
a sealing member configured to establish a sealed interface with the drive member, the drive member being movable relative to the sealing member from a first position to a second position, and a tightness of the sealed interface being different in the first position than in the second position,
wherein the sealed interface defines a sealed section of an interior of the drive unit housing, the mechanism interface is arranged within the sealed section and the coupler output portion is arranged outside of the sealed section, and
wherein the pump mechanism of the liquid handling unit comprises a pump driver operatively coupled to the coupler output portion of the drive member of the drive unit via a coupler input portion of the liquid handling unit.

11. The medical device of claim 10, wherein the liquid handling unit is releasably connected to the drive unit.

12. The medical device of claim 10, wherein the liquid handling unit comprises a liquid handling unit housing and the reservoir and the pump mechanism are arranged or retained in the liquid handling unit housing.

13. The medical device of claim 10, wherein the drive unit is a reusable unit and the liquid handling unit is a disposable unit.

14. The medical device of claim 10, wherein the medical device is a patch pump.

15. The medical device of claim 10, wherein the medical device is a drug delivery device and a liquid drug is retained in the reservoir.

16. The medical device of claim 10, wherein the pump mechanism is operable to move the liquid into the reservoir.

17. The medical device of claim 10, wherein the drive member is axially movable relative to the sealing member from the first position to the second position, and wherein the drive unit comprises a biasing mechanism configured to bias the drive member into the first position.

18. The medical device of claim 10, wherein the medical device comprises a mounting surface configured for mounting the medical device to a body of a mammal.

19. The medical device of claim 18, wherein the mounting surface is provided with an adhesive.

20. A method of administering a drug from a medical device into a subject, the method comprising:
administering the drug from a reservoir of a liquid handling unit of the medical device into the subject by a pump mechanism of the liquid handling unit, a pump driver of the pump mechanism of the liquid handling unit being operatively coupled to a coupler output portion of a drive member of a drive unit via a coupler input portion of the liquid handling unit,
wherein the medical device is configured such that the drive member of the drive unit is movable relative to a sealing member of the drive unit from (i) a first position in which a sealed interface between the sealing member and the drive member has a first tightness to (ii) a second position in which the sealed interface between the sealing member the drive member has a second tightness that is different from the first tightness, and
wherein a drive mechanism of the drive unit is coupleable to the drive member via a mechanism interface and configured to transfer a driving force or torque to the drive member for the pump mechanism to administer the drug from the reservoir, the mechanism interface is arranged within a sealed section defined by the sealed interface, and the coupler output portion is arranged outside of the sealed section.

21. The method of claim 20, wherein drug is used to treat one or more of the following disorders: diabetes mellitus, thromboembolism disorders, acute coronary syndrome, angina, myocardial infarction, cancer, macular degeneration, inflammation, hay fever, atherosclerosis, rheumatoid arthritis, or familial hypercholesterolemia.

* * * * *

UNITED STATES PATENT AND TRADEMARK OFFICE
CERTIFICATE OF CORRECTION

| | |
|---|---|
| PATENT NO. | : 12,005,230 B2 |
| APPLICATION NO. | : 17/054378 |
| DATED | : June 11, 2024 |
| INVENTOR(S) | : Michael Harms |

It is certified that error appears in the above-identified patent and that said Letters Patent is hereby corrected as shown below:

In the Claims

In Column 21, Line 44, Claim 10, after "section" insert -- , --

Signed and Sealed this
Thirtieth Day of July, 2024

Katherine Kelly Vidal
*Director of the United States Patent and Trademark Office*